United States Patent [19]
Fischer

[11] 3,986,863
[45] *Oct. 19, 1976

[54] AMINE FRUIT ABSCISSION AGENTS

[75] Inventor: Hanspeter Fischer, Bottmingen, Switzerland

[73] Assignee: Ciba-Geigy Corporation, Ardsley, N.Y.

[*] Notice: The portion of the term of this patent subsequent to Feb. 18, 1992, has been disclaimed.

[22] Filed: Dec. 4, 1974

[21] Appl. No.: 529,427

Related U.S. Application Data

[63] Continuation-in-part of Ser. No. 350,273, April 11, 1973, Pat. No. 3,867,127.

[52] U.S. Cl. ................................................ 71/121
[51] Int. Cl.² ............................................ A01N 9/20
[58] Field of Search ............... 71/121, 76, 86, 87, 71/103, 113, 114, 115

[56] References Cited
UNITED STATES PATENTS

| | | | |
|---|---|---|---|
| 3,065,066 | 11/1962 | McRae et al. | 71/70 |
| 3,460,936 | 8/1969 | Abramitis | 71/76 |
| 3,506,433 | 4/1970 | Abramitis et al. | 71/121 |
| 3,867,127 | 2/1975 | Fischer | 71/121 |
| 3,869,278 | 3/1975 | Wilcox | 71/121 |

OTHER PUBLICATIONS

Trebst et al., "Entkopphung der Photophosphorylierung etc.," (1966), 2, Naturforsch. 21, pp. 667–672, (1966).

*Primary Examiner*—Glennon H. Hollrah
*Attorney, Agent, or Firm*—Harry Falber

[57] ABSTRACT

This invention relates to a method for promoting the abscission of citrus fruit by means of octylamine and its addition salts as well as to compositions for this purpose.

3 Claims, No Drawings

AMINE FRUIT ABSCISSION AGENTS

CROSS REFERENCE

This is a continuation-in-part of my application Ser. No. 350,273, filed Apr. 11, 1973, now U.S. Pat. No. 3,867,127.

DETAILED DISCLOSURE

The present invention relates to a method for promoting the abscission of fruit of all kind, particularly citrus fruits, by means of the application of octylamine or of an acid addition salt thereof with an inorganic or organic acid to fruit bearing plants, as well as to compositions for this purpose, containing octylamine or one of its salts as active ingredient.

n-Octylamine is a known and readily available primary amine of formula $$CH_3-(CH_2)_7NH_2$$

m.w. 129.25; m.p. −5 to −1° C; 6.p 175°–177° C, a colourless liquid of density 0.782 $n_D^{20}$ 1.4290.

Suitable addition salts are preferably salts of strong mineral acids, such as hydrohalic acids e.g. hydrochloric acid, fluoboric acid ($HBF_4$), nitric acid, phosphoric acid, thio- or dithiphosphoric acids or sulfuric acid; or organic acids such as benzoic acid, halobenzoic acids, cinnamic acid and substituted cinnamic acids, naphthoic acids, phthalic acid, acetic acid, haloacetic acids, propionic acid, halopropionic acids, butyric acid, lactic acids, stearic acid, oxalic acid, tartaric acid, maleic acid, etc..

The herbicidal and plant-growth-regulating applications of amines for the purpose of increasing resistance to frost and improving fruit setting have been mentioned in the U.S. Pat. Specification No. 3,460,936, in the French Patent Specification No. 1,375,967, as well as in the German Patent Specification No. 1,032,023. The inhibition of lateral shoots on plants, e.g. on tobacco, soya bean and cotton plants, is described in the U.S. Patent Specifications Nos. 3,223,514 and 3,506,433, and also in the German 'Offenlegungsschrift' No. 2,121,009. The defoliating action of amines in cotton crops is described in the U.S. Patent Specification No. 3,056,066 and in the French Patent Specification No. 1,032,967.

At the amounts applied, n-Octylamine or its salts are harmless to all kinds of higher life. Primary alkylamines with more than 7 carbon atoms in the alkyl chain have been observed to prevent the germination of bacterial spores, see L. J. Rode and J. W. Foster, "Germination of Bacterial spores with Alkyl Primary Amines" J. Bacteriology 81 p 768–779 (1961). Application of octylamine onto fruits to be harvested has the further advantage to protect these fruit to some extent from attack by microorganisms.

Tests have shown that octylamine and its acid addition salts are particularly valuable for the promotion of fruit abscission in the case of citrus crops. Preferred are addition salts of inorganic acids, especially of hydrohalic acids.

With regard to the practical application, the active substance has to be applied in an amount which effects the promotion of fruit abscission but which does not produce defoliation to an exaggerated extent.

Some leaves will always fall during harvest period since the life-span of a leaf on a fruit tree is limited. Some species of fruit trees loose their leaves every year and defoliation during harvest period occurs naturally. Others keep their leaves for several years and there is partial regeneration of leaves during harvest period. See Mc C. D. Carty, WC Kemper and L.N. Lewis "Leaf and twig removal as related to mechanical harvesting of oranges" in the Calif. Citrograph 50 p 208 (1965).

The promotion of fruit abscission on citrus fruits is illustrated by the following tests.

Octylamine was sprayed, as solution in the given concentration, until runoff onto branches well hung with at least 10 fruits on various orange trees of different varieties. The results of the tests are evaluated 7 days later by the method developed by W. C. Wilson and C. H. Hendershott [Proc. Am. Soc. Hort. Sci. 90, 123–129 (1967)]. Each test was repeated 2–3 times on different trees. The force to be applied to effect abscission of the fruit is measured; the results are expressed in the following tables as percentages of the respective force measured in the case of the untreated control fruit. The amount of defoliation observed during the test is also indicated. The tests were made at various locations and dates with different varieties of citrus fruit.

Test No. 1: country: USA
fruit: Orange "Pineapple"
treatment: January 7, 1972
evaluation: January 14, 1972

Test No. 2: country: South Africa
fruit: Orange "Valencia"
treatment: August 6, 1972
evaluation: August 13, 1972

Test No. 3: country: Spain
fruit: Orange "Salustiana"
treatment: December 28, 1972
evaluation: January 13, 1973

Test No. 4: country: South Africa
fruit: Orange "Navel"
treatment: May 8, 1973
evaluation: May 15, 1973

Test No. 5: country: South Africa
fruit: Orange "Valencia"
treatment: June 22, 1973
evaluation: June 29, 1973

Test No. 6: country: Spain
fruit: Orange "Navel"
treatment: December 6, 1973
evaluation: December 13, 1973

Test No. 7: country: Spain
fruit: Orange "Salustiana"
treatment: December 20, 1973
evaluation: December 27, 1973

Test No. 8: country: South Africa
fruit: Orange "Valencia"
treatment: July 12, 1974
evaluation: July 19, 1974

The results are summarized in the table below.

| Test No. | concentration of octylamine in solution applied | mean force required to effect abscission | reduction of force compared to that of untreated control | defoliation % of leaves fallen |
|---|---|---|---|---|
| 1 | 4000 ppm | 0,5 kg | 95% | 10 |
|   | 2000 ppm | 0,5 kg | 95% | 5 |
|   | untreated | 8,5 kg | — | 0 |
| 2 | 4000 ppm | 2,6 kg | 73% | 0 |

-continued

| Test No. | concentration of octylamine in solution applied | mean force required to effect abscission | reduction of force compared to that of untreated control | defoliation % of leaves fallen |
|---|---|---|---|---|
|   | 3000 ppm | 4,9 kg | 50% | 5 |
|   | 2000 ppm | 8,0 kg | 18% | 0 |
|   | untreated | 9,8 kg | — | 0 |
| 3 | 4000 ppm | 4,7 kg | 48% | 12 |
|   | 2000 ppm | 7,1 kg | 21% | 0 |
|   | 1000 ppm | 8,1 kg | 10% | 0 |
|   | untreated | 9,0 kg | — | 0 |
| 4 | 4000 ppm | 4,1 kg | 45% | 3 |
|   | 2000 ppm | 4,8 kg | 35% | 0 |
|   | 1000 ppm | 5,9 kg | 20% | 0 |
|   | untreated | 7,4 kg | — | 0 |
| 5 | 4000 ppm | 2,0 kg | 71% | 2 |
|   | 2000 ppm | 3,5 kg | 49% | 0 |
|   | 1000 ppm | 3,9 kg | 43% | 0 |
|   | untreated | 6,8 kg | — | 0 |
| 6 | 3000 ppm | 4,0 kg | 58% | 0 |
|   | 2000 ppm | 5,5 kg | 42% | 0 |
|   | 1000 ppm | 6,9 kg | 27% | 0 |
|   | untreated | 9,5 kg | — | 0 |
| 7 | 4000 ppm | 3,2 kg | 66% | 17 |
|   | 3000 ppm | 5,6 kg | 41% | 2 |
|   | 2000 ppm | 7,0 kg | 26% | 0 |
|   | untreated | 9,4 kg | — | 0 |
| 8 | 3000 ppm | 2,0 kg | 72% | 6 |
|   | 1500 ppm | 3,3 kg | 54% | 3 |
|   | untreated | 7,1 kg | — | 2 |

Octylamine or its salts are used in the forming of aqueous suspensions, emulsions and solutions, which are obtained from active-substance concentrates in the form of a. wettable powders and
b. emulsion concentrates.

Compositions according to the invention are produced in a manner known per se by the intimate mixing and/or grinding of active substances of the general formula I with suitable carriers, optionally with the addition of dispersing agents or solvents which are inert to the active substances. The active substances. The active substances can be obtained and used in the following forms:

water-dispersible active-substance concentrates:

wettable powders and emulsifiable concentrates; liquid preparations:-solutions.

Water-dispersible concentrates of active substances, i.e. wettable powders and emulsifiable concentrates, are agents which can be diluted with water to obtain any desired concentration. They consist of active substance, carrier optionally additives which stabilise the active substance, surface-active substances, antifoam agents and, optionally, solvents. The concentration of active substance in these agents is between 5 and 80%.

The wettable powders and pastes are obtained by the mixing and grinding of the active substances with dispersing agents and pulverulent carriers, in suitable devices, until homogeneity is obtained. Suitable carriers are, e.g. kaolin, talcum, bole, loess, chalk, limestone, ground limestone, attapulgite, dolomite, diatomaceous earth, precipitated silicic acid, alkaline-earth silicates, sodium and potassium aluminium silicates (feldspars and mica), calcium and magnesium sulphates, magnesium oxide, ground synthetic materials, fertilisers such as ammonium nitrate, urea, ground vegetable products such as bran, bark dust, sawdust, ground nutshells, cellulose powder, residues of plant extractions, active charcoal, etc., single or in admixture with each other. As dispersing agents it is possible to use, e.g. condensation products of sulphonated naphthalene and sulphonated naphthalene derivatives with formaldehyde, condensation products of naphthalene or of naphthalene-sulphonic acids with phenol and formaldehyde, as well as alkali, ammonium and alkaline-earth metal salts of ligninsulphonic acid, also alkylarylsulphonates, alkali metal salts and alkaline-earth salts of dibutyl naphthalenesulphonic acid, fatty alcohol sulphates such as salts of sulphated hexadecanols, heptadecanols, octadecanols, and salts of sulphated fatty alcohol glycol ethers, the sodium salt of oleyl methyl tauride, ditertiary ethylene glycols, dialkyl dilauryl ammonium chloride, and fatty acid alkali-metal and alkaline-earth metal salts.

Suitable antifoam agents are, for example, silicones.

The active substances are so mixed, ground, sieved and strained with the above mentioned additives that the solid constituent in the case of wettable powders has a particle size not exceeding 0.02 to 0.04 mm. For the preparation of emulsion concentrates, dispersing agents are used such as those mentioned in the preceding paragraphs, organic solvents and water. Suitable solvents are, e.g. alcohols, benzene, xylenes, toluene, dimethylsulphoxide, N,N-dialkylated amides, N-oxides of amines, particularly trialkylamines, and mineral oil fractions boiling in the range of 120° to 350° C. The solvents must be practically odourless, non-phytotoxic, inert to the active substances and not readily combustible.

Furthermore, the agents according to the invention can be used in the form of solutions. For this purpose, the active substance (or several active substances) of the general formula I is (or are) dissolved in water, or in suitable organic solvents, solvent mixtures, or mixtures of organic solvents with water. As organic solvents it is possible to use aliphatic and aromatic hydrocarbons, their chlorinated derivatives, alkylnaphthalenes, mineral oils on their own or in admixture with each other. The solutions should contain the active substance in concentrations of from 1 to 20%.

For preservation purposes, it is possible to add to the described agents according to the invention other biocidal active substances or agents; for example: fungicides, bactericides, fungistatics or bacteriostatics. The agents according to the invention may also contain trace elements, and so forth.

The procedure for the producing of preparations of octylamine and its acid addition salts is described in the following. The term 'parts' denotes parts by weight.

Wettable powders

The following substances are used for the preparation of 25% wettable powders:

a.
25 parts of octylamine
8 parts of a mixture of nonylphenolpolyoxyethylene and calcium dodecylbenzenesulphonate,
2 parts of octylphenoxyethylene glycol with 9 to 10 moles of ethylene oxide per mole of octylphenol,
5 parts of silicic acid,
60 parts of kaolin;

b.
25 parts of octylamine
8 parts of a mixture of nonylphenolpolyoxyethylene and calcium dodecylbenzenesulphonate,
2 parts of octylphenoxyethylene glycol with 9 to 10 moles of ethylene oxide per mole of octylphenol,
10 parts of silicic acid,
55 parts of kaolin;

c.
25 parts of active octylamine
25 parts of silicic acid,
5 parts of naphthalenesulphonic acid/phenolsulphonic acid/formaldehyde condensate 3:2:1,
5 parts of sodium dibutylnaphthylsulphonate,
40 parts of kaolin;

d.
25 parts of active octylamine
7.5 parts of silicic acid,
5.3 parts of octylphenol-octaglycol ether,
2.2 parts of 1-benzyl-2-stearyl-benzimidazole-6,3'-disulphonic acid sodium,
0.5 part of oleic acid,
59.5 parts of bolus alba.

The octylamine is absorbed onto the appropriate carriers (kaolin and bolus), and the whole subsequently mixed and ground. Wettable powders are obtained which possess excellent wettability and suspension properties. It is possible to prepare from such wettable powders, by dilution with water, suspensions of any desired concentration of active substance. Emulsifiable concentrate The following constituents are mixed together in the preparation of 25% emulsifiable concentrates:

a.
250 g of octylamine HCl
10 g of octylphenoxyethylene glycol with 9 to 10 moles of ethylene oxide per mole of octylphenol,
250 g of methanol,
ad 1000 ml of water;

b.
250 g of octylamine HCl
100 g of a mixture of alkylarylsulphonate and alkylarylpolyglycol ether,
ad 1000 ml of xylene;

c.
250 g of octylamine HCl
100 g of a mixture of alkylarylsulphonate and alkylarylpolyglycol ether,
ad 1000 ml of xylene;

d.
250 g of octylamine HCl
100 g of emulsifier (G-3634 A),
ad 1000 ml of benzyl alcohol;

e.
250 g of octylamine HCl
100 g of emulsifier (G-3634 A),
ad 1000 ml of benzyl alcohol.

This concentrate can be mixed with water to form emulsions of suitable concentrations.

Solutions:

250 g of octylamine or one of its salts is dissolved in 1000 ml of water. Before application, this solution can be diluted with water to any suitable concentration.

I claim:

1. A method for the promotion of the abscission of citrus fruit which comprises applying to fruit bearing plants an effective amount of octylamine or octylamine hydrochloride.

2. The method according to claim 1 which comprises applying to fruit bearing citrus plants an effective amount of octylamine.

3. The method according to claim 1 which comprises applying to fruit bearing citrus plants an effective amount of octylamine hydrochloride.

* * * * *